(12) United States Patent
Coombs

(10) Patent No.: US 7,822,180 B2
(45) Date of Patent: Oct. 26, 2010

(54) METHODS AND APPARATUS FOR BATTERY POWERED DEVICES

(75) Inventor: Kevin Andrew Coombs, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 958 days.

(21) Appl. No.: 11/622,594

(22) Filed: Jan. 12, 2007

(65) Prior Publication Data

US 2008/0170666 A1 Jul. 17, 2008

(51) Int. Cl.
*H05G 1/08* (2006.01)
*H05G 1/10* (2006.01)
*H05G 1/26* (2006.01)

(52) U.S. Cl. ............... 378/115; 378/91; 378/92; 378/98; 378/102; 378/114; 378/116; 378/198

(58) Field of Classification Search ............ 378/91, 378/92, 98, 98.8, 101, 102, 103, 114, 115, 378/116, 117, 189, 198
See application file for complete search history.

(56) References Cited

U.S. PATENT DOCUMENTS

| 4,553,081 | A |  | 11/1985 | Koenck |  |
|---|---|---|---|---|---|
| 4,797,907 | A |  | 1/1989 | Anderton |  |
| 4,947,123 | A |  | 8/1990 | Minezawa |  |
| 4,952,862 | A |  | 8/1990 | Biagetti et al. |  |
| 5,278,487 | A |  | 1/1994 | Koenck |  |
| 5,317,269 | A |  | 5/1994 | Mills et al. |  |
| 5,394,089 | A |  | 2/1995 | Clegg |  |
| 5,530,362 | A |  | 6/1996 | Boehm et al. |  |
| 6,859,521 | B2 | * | 2/2005 | Spahn | 378/117 |
| 7,016,467 | B2 | * | 3/2006 | Brooks | 378/102 |
| 7,197,112 | B2 | * | 3/2007 | Maschke | 378/91 |
| 7,346,422 | B2 | * | 3/2008 | Tsuchiya et al. | 700/168 |
| 7,382,859 | B2 | * | 6/2008 | Nokita et al. | 378/98.8 |
| 7,598,842 | B2 | * | 10/2009 | Landram et al. | 340/5.73 |
| 2006/0181243 | A1 | * | 8/2006 | Graves et al. | 320/116 |
| 2008/0312852 | A1 | * | 12/2008 | Maack | 702/63 |
| 2009/0232278 | A1 | * | 9/2009 | Ohara | 378/116 |

FOREIGN PATENT DOCUMENTS

WO   WO 2004/082894 A1 *   9/2004

* cited by examiner

*Primary Examiner*—Allen C. Ho
(74) *Attorney, Agent, or Firm*—ZPS Group, SC

(57) ABSTRACT

A method includes automatically determining a specific mobile device to use from a plurality of mobile devices based on at least one of a battery metric, a patient procedure, and a location of the devices or of the patient.

21 Claims, 2 Drawing Sheets ated with reference to the figures wherein similar num-
METHODS AND APPARATUS FOR BATTERY POWERED DEVICES

BACKGROUND OF THE INVENTION

This invention relates generally to battery powered devices, and more particularly, to methods and apparatus that provide for the displaying of battery status.

Many different devices including mobile x-ray imaging devices are battery powered. A user must thus plan his or her work based on the amount of charge remaining in the device's batteries. Typically, a state of charge (SOC) is shown using a bar graph or a numerical percentage of the total charge of a fully charged battery. However, this percentage can be difficult for the user to interpret. For example, when the batteries in a device are older, the bar graph will decrease at a faster rate. This battery rate drain change is unknown to the user until it happens. Experienced users may be able to translate the number of bars remaining into a usable format in their heads, but an inexperienced or infrequent user may not be able to make the translation.

It would therefore be desirable to, instead of displaying to the user that the percentage of total battery charge, but rather, to display a device specific metric related to battery life wherein the metric is other than the percentage of total battery charge. Additionally, some facilities have multiple mobile devices with different levels of charge and it would be desirable to be able to match specific devices based on each device's charge level and location in a facility to specific exams at specific locations.

BRIEF DESCRIPTION OF THE INVENTION

In one aspect, a method includes automatically determining a specific mobile device to use from a plurality of mobile devices based on at least one of a battery metric, a patient procedure, and a location of the devices or of the patient.

In another aspect, a computer readable medium is embedded with a program configured to instruct the computer to receive indications of a plurality of imaging systems' battery's statuses, and schedule examinations and re-chargings at least partially based on the received indications.

In yet another aspect, a mobile x-ray imaging system includes an x-ray source, an x-ray detector positioned to receive x-rays emitted from the source, a computer operationally coupled to the x-ray detector and the x-ray source, and a battery providing power to the x-ray source, the x-ray detector, and the computer, wherein the computer is configured to determine a status of the battery and communicate the determined status to at least one of another mobile x-ray imaging system and a central controller.

DETAILED DESCRIPTION OF THE INVENTION

There are herein described methods and apparatus useful for battery powered devices such as, for example but not limited to imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of an x-ray system, it is contemplated that the benefits of the invention accrue to all imaging systems and modalities such as CT, PET, MRI, SPECT, Ultrasound, fused systems such as a CT/PET system, and/or any modality yet to be developed in which rechargeable batteries are used. Although described in a medical imaging setting it is contemplated that the benefits apply to all battery operated devices even including those with replaceable batteries. As used herein, the phrase battery life refers to the point at which the battery will not have sufficient power to perform an intended function. The term battery life does not refer to the point where the battery would be thrown out unless it is specifically mentioned with reference to a non-rechargeable battery, and it is then called disposal life.

Figure 1:
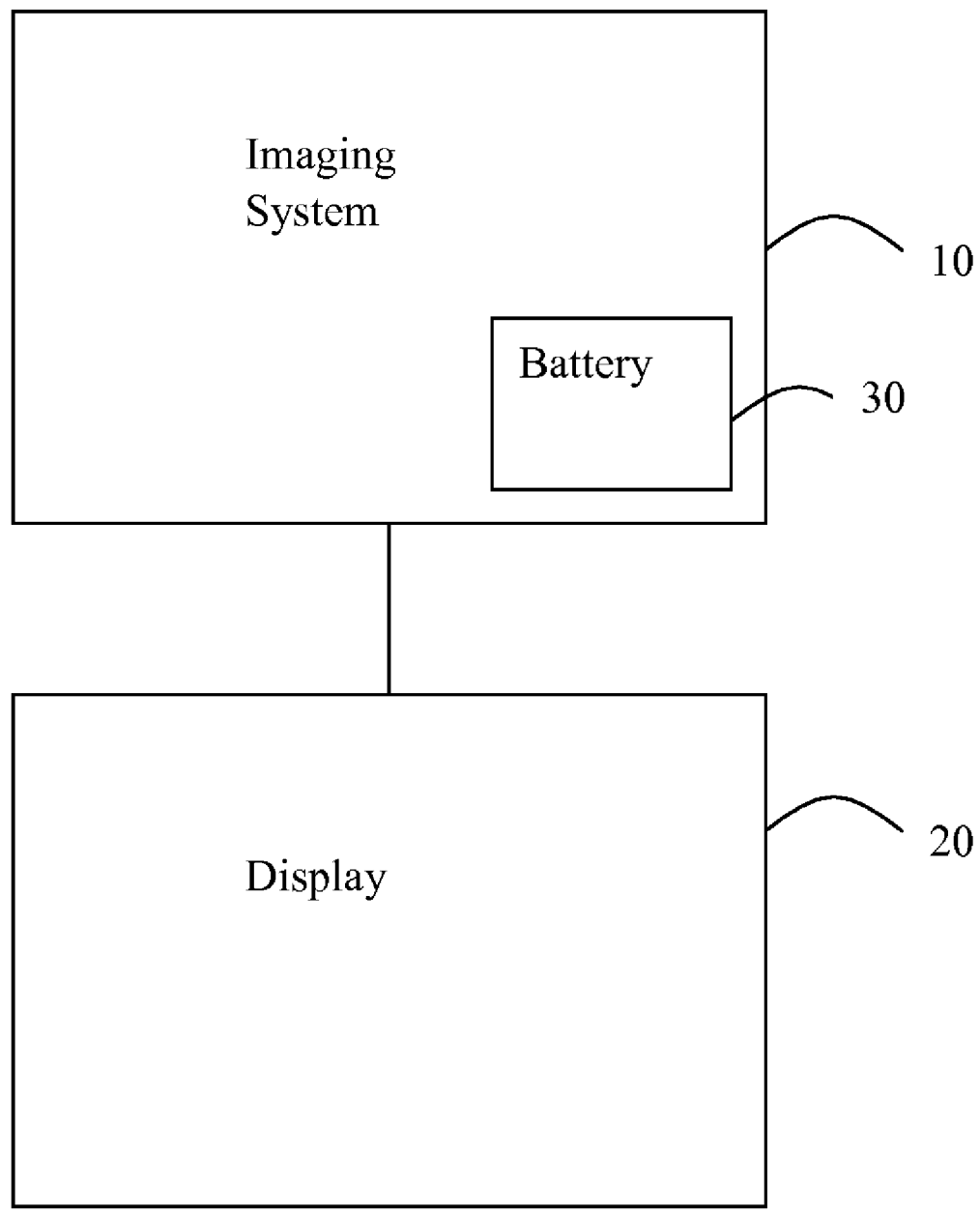
FIG. 1 illustrates a block diagram of an exemplary imaging system.

FIG. 1 illustrates an imaging system 10 with an associated display 20. Imaging system 10 can be of any modality, but in one embodiment, system 10 is an x-ray system. In another embodiment, system 10 is a dual modality imaging system such as a combined CT/PET system and the below described obtainment/attainment of a non-scanner dependent patient specific metric can be done in one modality (e.g., CT) and the processed data can be transferred to the other modality (e.g., PET). Display 20 can be separate from system 10 or integrated with system 10. System 10 includes an acquisition device such as an x-ray radiation detector. System 10 also includes a rechargeable battery 30. System 10 may be a mobile imaging system shaped substantially in a C-arm or O-arm shape as is known in the art for some mobile imaging systems. Fundamentally, the herein described methods and apparatus display the charge remaining to a user in any application-specific unit. In a mobile x-ray imaging system embodiment, this could be in terms of exams remaining, drive time remaining, idle time remaining, or any other unit applicable to the operator's process. The "exams remaining" unit could be typical exams remaining, which would mean using an average of different exam types, or it could be specific exams remaining, which would reference a particular type of exam. The units displayed can be calculated based on actual battery voltages, measured battery discharge, or calculated battery discharge.

All potential application-specific units can be calculated using either static equations, or dynamic equations that are generated by the system after observing actual user processes and usage. Another way to state this is that the system learns how the user was using the system, and calculates the reporting parameters accordingly. In addition, the total charge may possibly change over time and this may be monitored as well. It is important to note that user history can be static or dynamic and static history can be factory static or user static. For example, factory static means that the manufacturer manufactures every system with an initial average for the event numbers to be displayed. And user static means that a particular device keeps track of the battery life over a sufficient number of cycles to determine an average and then the device uses that average to display the device specific battery metric. While user dynamic is similar to user static, user dynamic continues to keep track of the battery life over further cycles and repeatedly updates the average which is used to display the application-specific units or specific battery metric. Note that both for the user static and the user dynamic methods, the system may initially be programmed with the factory static.

Besides displaying this information to the user, this information could also be used by scheduling systems or personnel to decide which imaging systems are available to handle a given exam prescription as described in greater detail below.

The inverse case of what is described above is also disclosed herein. This is to indicate the remaining recharge time of a rechargeable battery in a battery operated device or system, in units of time or other application-specific parameter. As in the discharge case, this information is also useful for scheduling systems or personnel to decide which imaging systems are available to handle a given exam prescription. Additionally, in one embodiment, the user is able to input a plurality of specific exam types, and/or protocols and the system determines the expected discharge or recharge time given the series of events which were inputted. In other words, and in one example, a user wishes to do two cardiac calcification scans, one lung polyp scan, and two ischemic versus infracted brain tissue scans. Each individual scan may be done with different parameters. The imaging system receives the information and determines if sufficient battery life remains to perform all the scans without performing a recharge of the apparatus and can also display that if the system is recharged for X minutes, then the charge is sufficient to complete all the planned scans. Additionally and quite useful in the embodiments in which multiple imaging systems are available, and wherein the imaging systems are networked, the planning for all systems may be done remotely by computer and/or with support from a person whose job is to schedule system usage. In the ER situation where workflow is less scheduled ahead, as exam requests are entered into a computer on a computer network, the scheduling computer can then work a new exam into the existing workflow and reschedule subsequent exams as to which system will be used in what order or location to minimize downtime of both the systems and personnel. In other words, by having an application-specific unit or metric that is also device specific to each imaging systems's battery life, this enables more efficient scheduling of the imaging systems. Moreover, herein enabled is the ability to more easily integrate new workflow into existing workflow based on expected battery life.

The imaging system includes a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. The detector may be a flat panel solid-state image detector, for example, although conventional film images stored in digital form in the memory may also be processed. In one embodiment, the processing circuit executes instructions stored in firmware (not shown).

The system 10 described above is configurable, such that a user may select from a plurality of application-specific units to display, depending upon what the user is interested in using the system. For example, if a user has to drive a system from one location to another, he/she may select to display the amount of remaining drive time. Alternatively, if a user is interested in performing a series of imaging exams, he/she may select to display the number of exams remaining. These lists and selections may be available at the system's display or available at a display of a networked computer.

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research. Although the herein described methods are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 2:
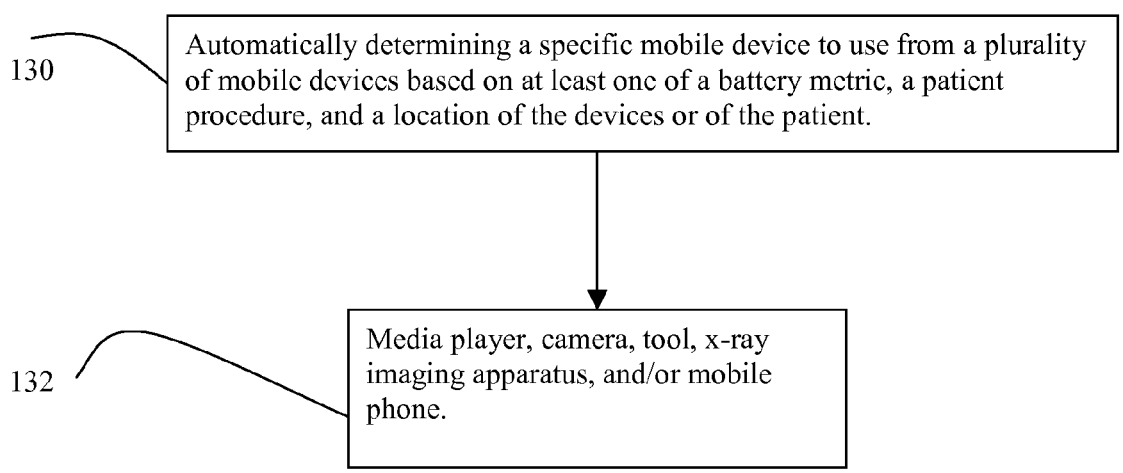
FIG. 2 illustrates a method including the step of automatically determining a specific mobile device to use from a plurality of mobile devices based on at least one of a battery metric, a patient procedure, and a location of the devices or of the patient.

FIG. 2 illustrates a method 130 including the step of automatically determining a specific mobile device to use from a plurality of mobile devices based on at least one of a battery metric, a patient procedure, and a location of the devices or of the patient. FIG. 2 also illustrates that method 130 may be implemented into a user operated battery powered device 132.

Instead of just displaying to a user the remaining capacity of the battery, the herein described methods and apparatus provide for automatically determining which device is to be dispatched to a patient, based on the procedures to be performed on that patient, the remaining battery capacity, the current location of the device, and/or the location where the procedure on the patient will be performed. In one embodiment, a central scheduler (such as, for example, a hospital information system or a radiology information system (HIS/RIS)) intelligently dispatches any given exam to the appropriate mobile device based on location, remaining capacity, and any other relevant factors (such as other exams that need to be performed). Another embodiment removes the central controller, and lets all of the devices within the hospital "negotiate" with each other to determine which device should perform the exam. Additionally, the herein described methods and apparatus are applicable to any plurality of mobile devices. For example, a company may have a collection of laptop computers, which it enables employees to check out and the scheduling of these "checkings out" can be done based on battery life and intended application or other metric. Another company could have a collection of phones either the walkie-talkie type or cell phones that are checked out-able. These are all intended to be illustrative examples and not limiting because it is contemplated the benefits the invention accrue to all mobile devices which have batteries.

Once the exam has been dispatched and the exam start time is within a certain window, the unit selected for the exam would indicate to nearby staff that it needs to be operated by blinking a light, sounding a tone, or by some other means.

Figure 3:
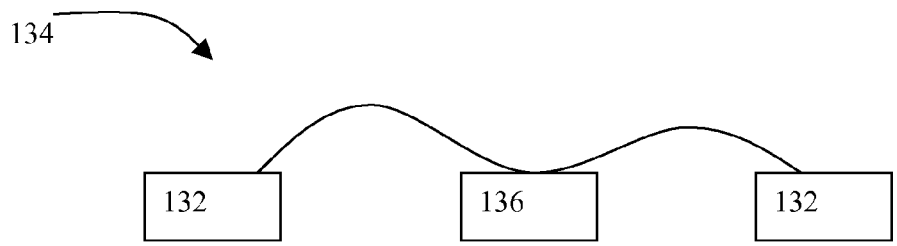
FIG. 3 illustrates a diagram of a network with at least two imaging apparatuses coupled to at least one computer.

FIG. 3 illustrates a network 134, including at least two mobile imaging apparatuses 132 operationally coupled to at least one computer 136, which in one embodiment is a scheduling or planning computer that schedules usage of the imaging apparatuses. The apparatus scheduling is based on at least one of an application-specific battery metric, a procedure to be performed using the apparatus, and a location of the apparatus or of the patient.

In one embodiment a user operative device including a battery, wherein the device is configured to display device specific metric related to battery life wherein the metric is other than a percentage of total battery charge is provided. The device may be a mobile phone such as a cell phone or a cordless phone. The device may be a computer, and the device may be a tool. The device may be a media player, and different features may or may not be included, depending on the specific implementation. For example, if the device is a camera, the device specific metric could be the number of pictures remaining without a recharge. This can be figured with or without the user using the flash capability or could be done using an average of flash versus non-flash based upon the specific user's history. The metric could be based upon for many parameters. In the mobile phone example, the number could be the number of talk minutes, it could be the number of standby minutes, it could be the average life based upon a mixture of talk versus standby, this may or may not be based upon the user's specific past history, the metric could factor in volumes such as speaker volume and microphone volume or any of many other parameters that would affect battery life. Again, with respect to mobile phones, an example of factory static would be programming the phone to report a set number of phone calls remaining based on a set amount of charge in the battery, and using multiples thereof. X=AB, is an example equation, wherein X is the number of calls displayed as remaining, A is a factory set number, and B is the number of units of discreet charge in the battery. In this example, A can adaptively change to the user's usage history, if dynamic history is desired.

In the embodiment where the device is capable of playing media, the media may be audio and/or video and the metric could be the number of songs remaining. The audio number can be based on user history, and the video number may also be based on user history. The metric may be adjusted for other battery life adjustment factors such as the brightness of the video display, the volume of the speakers, and/or any other factor that affects battery life.

Another embodiment, the device is a computer and the device specific metric could be time remaining, it could be based on how the computer is currently configured with the current software. The computer could be configured to suggest to the user to eliminate certain applications such as Internet browsing or word processing and/or to ask a user to select which is most important, and similar to the scheduling of multiple x-ray mobile units in a network hospital setting, with the computer implementation, it could analyze the different power demands created by the different programs and then schedule the programs to run in order to maximize battery life. This is an example of an application specific metric. Another example would be to display to the user different applications and different times (word-processing-1.5 hours; watching a video-55 minutes, etc.). In addition, of course it could be any other battery life dependent factor. In the tool embodiment, the tool may be a cutting tool, a drilling tool, a screw-driving tool, or a nailing tool. Other tools or devices include hand-held vacuums.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Technical effects include more efficient scheduling of scans, informing users how many songs they can play, and informing users how many minutes they can use their phones for.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising:
    determining, for each of a plurality of imaging systems, a charge remaining in a battery associated with the respective imaging system;
    receiving an input regarding at least one scan to be performed on a subject;
    determining an expected battery discharge associated with the at least one scan;
    identifying an imaging system capable of performing the at least one scan based on the expected battery discharge associated with the at least one scan and the charge remaining in the respective batteries of each of the plurality of imaging systems;
    scheduling the at least one scan on the identified imaging system at a desired time; and
    performing the at least one scan on the identified imaging system at the desired time.

2. The method of claim 1 further comprising identifying the imaging system capable of performing the at least one scan based on at least one of a location of the subject and a location of each of the plurality of imaging systems.

3. The method of claim 1 further comprising, for each of the plurality of imaging systems, displaying the charge remaining in the battery in an application-specific unit.

4. The method of claim 3 wherein the application specific unit comprises one of exams remaining, drive time remaining, and idle time remaining.

5. The method of claim 1 wherein determining the charge remaining in the battery associated with each of the plurality of imaging systems comprises determining the charge based on one of a battery voltage, a measured battery discharge, and a calculated battery discharge.

6. The method of claim 1 further comprising determining a recharging time needed to recharge the battery associated with each of the plurality of imaging systems based on the determined charge remaining in each battery.

7. The method of claim 1 further comprising:
    receiving an additional input regarding additional scans to be performed;
    rescheduling the at least one scan on the identified imaging system or on one of the other of the plurality of imaging systems based on the additional input.

8. The method of claim 1 further comprising alerting an operator to begin the at least one scan at the scheduled time for performing the at least one scan.

9. The method of claim 1 further comprising negotiating between each of the plurality of imaging systems to identify the imaging system capable of performing the at least one scan and to schedule the at least one scan to be performed.

10. The method of claim 1 wherein receiving the input, identifying the imaging system capable of performing the at least one scan, and scheduling the at least one scan is performed by a central control system networked with the plurality of imaging systems.

11. A non-transitory computer readable storage medium having a computer program stored thereon and representing a set of instructions that when executed by a computer causes the computer to:
   receive an input from each of a plurality of imaging systems, the input from each of the plurality of imaging systems indicative of a charge remaining in a battery associated with a respective imaging system, and wherein the charge remaining is defined in an application-specific unit specific to the imaging system;
   receive an input regarding at least one scan to be performed on a subject;
   determine an expected battery discharge associated with the at least one scan;
   identify an imaging system capable of performing the at least one scan based on the expected battery discharge associated with the at least one scan and the charge remaining in the respective batteries of each of the plurality of imaging systems;
   schedule the at least one scan on the identified imaging system, such that the identified imaging system performs the at least one scan at a desired time.

12. The non-transitory computer readable storage medium of claim 11 wherein the set of instructions further causes the computer to identify the imaging system capable of performing the at least one scan based on at least one of a location of the patient and a location of each of the plurality of imaging systems.

13. The non-transitory computer readable storage medium of claim 11 wherein the set of instructions further causes the computer to determine a recharging time needed to recharge the battery of each of the plurality of imaging systems based on the received input indicative of the charge remaining in each respective battery.

14. The non-transitory computer readable storage medium of claim 13 wherein the set of instructions further causes the computer to identify the imaging system capable of performing the at least one scan based on the determined recharging time of each respective battery.

15. The non-transitory computer readable storage medium of claim 11 wherein the application-specific unit specific to the imaging system comprises one of exams remaining, drive time remaining, and idle time remaining.

16. A mobile x-ray imaging system comprising:
   an x-ray source;
   an x-ray detector positioned to receive x-rays emitted from the x-ray source;
   a computer operationally coupled to said x-ray detector and said x-ray source; and
   a battery providing power to the x-ray source and the x-ray detector;
   wherein the computer is programmed to:
      determine a status of the battery indicative of a charge remaining in the battery;
      receive an input regarding at least one scan to be performed by the mobile x-ray imaging system;
      determine an expected battery discharge associated with the at least one scan;
      determine if the charge remaining in the battery is sufficient to allow the mobile x-ray imaging system to perform the at least one scan; and
      if the charge remaining in the battery is determined to be sufficient, then schedule the at least one scan to be performed on the mobile x-ray imaging system.

17. The mobile x-ray imaging system of claim 16 further comprising a display; and
   wherein the computer is further programmed to cause the display to display the charge remaining in the battery in an application-specific unit, the application specific unit comprising one of exams remaining, drive time remaining, and idle time remaining.

18. The mobile x-ray imaging system of claim 16 wherein the computer is further programmed to determine the status of the battery based on one of a battery voltage, a measured battery discharge, and a calculated battery discharge.

19. The mobile x-ray imaging system of claim 16 wherein the computer is further programmed to determine a recharging time needed to recharge the battery based on the determined status of the battery.

20. The mobile x-ray imaging system of claim 16 wherein, if the charge remaining in the battery is determined to not be sufficient, the computer is further programmed to communicate with at least one other mobile x-ray imaging system in operative communication therewith, so as to schedule the at least one scan on one of the at least one other mobile x-ray imaging systems.

21. The mobile x-ray imaging system of claim 16 wherein the computer is further programmed to:
   receive an input that the at least one scan needs to be rescheduled; and
   automatically reschedule the at least one scan.

* * * * *